United States Patent [19]

Guillou et al.

[11] Patent Number: Plant 7,360

[45] Date of Patent: Oct. 16, 1990

[54] VARIETY OF GERANIUM NAMED NANETTE

[75] Inventors: Jacques Guillou; Bernard Guillou; Maurice Guillou, all of Saint-Malo, France

[73] Assignee: Etablissement Guillou Freres Jacques, Bernard et Maurice, France

[21] Appl. No.: 359,170

[22] Filed: May 31, 1989

[51] Int. Cl.[5] ..... A01H 5/00

[52] U.S. Cl. ..... Plt./68

[58] Field of Search ..... Plt./68

*Primary Examiner*—Howard J. Locker

*Attorney, Agent, or Firm*—Webb, Burden, Zieseheim & Webb

[57] ABSTRACT

A new and distinct variety adds a new color to the Ivy Geranium class. The "Geranium" red color accents the medium green foliage. This variety is also much hardier in higher temperatures than those Ivy Geraniums currently on the market.

No Drawings

BACKGROUND OF THE NEW PLANT

The present invention comprises a new and distinct cultivar of *Pelargonium*×*peltatum* known by the varietal name Nanette (Oglevee Ltd. No. 7039, French No. 581 Guitari). The new variety was discovered in a selective breeding program by Messrs. Jacques, Maurice and Bernard Guillou. The new variety is a selection from the crossing of No. 14×Moulin Rouge. The new variety has shorter and better quality cuttings than its parentage.

The new cultivar was discovered in 1985 at 55 rue Godard, 35400 Saint-Malo, France, was first asexually reproduced by cuttings during 1986 and 1987 at Saint-Malo, France, and more recently has been repeatedly asexually reproduced by cuttings at Oglevee Ltd. in Connellsville, Pa. It has been found to retain its distinct characteristics through successive propagations.

The new cultivar, when grown in a glass greenhouse in Connellsville, Pa., using full light, 60° F. temperature, 68° F. day temperature, 71° F. vent temperature, and grown in a soilless media with constant fertilizer of 200–250 parts per million nitrogen and potassium, has a response time from a rooted cutting to a flowering plant in a four inch (10 cm) pot of six weeks.

DESCRIPTION OF THE DRAWING

The accompanying drawing illustrates a new cultivar, the color being as true as possible with color illustrations of this type.

DESCRIPTION OF THE NEW PLANT

The following detailed descriptions set forth the characteristics of the new cultivar. The data which define these characteristics were collected from asexual reproductions carried out by Oglevee Ltd. in Connellsville, Pa. The plants were started as rooted cuttings which were potted on Aug. 1, 1988 and flowered on Sept. 15, 1988. These 10 cm pots were potted into a 26 cm hanging basket and maintained until Mar. 4, 1989 when the color readings were taken. The plant histories were taken of plants blossomed under full light in a greenhouse and color readings were taken indoors under 200–220 foot candles of cool white fluorescent light. Color references are primarily to the R.H.S. Colour Chart of The Royal Horticultural Society of London.

THE PLANT

Classification:

*Botanical.*—*Pelargonium*×*peltatum.*

*Commercial.*—Ivy Geranium (#7039) Nanette.

Form: Cascading mound.

Height: 20–26 cm from media surface.

Growth: Free branching, free and early flowering; upright mound with cascading side growth.

Strength: Holds an upright mound shape without support while allowing outer branches to cascade.

Foliage: Stalked leaf attachment; no zone present.

Leaves:

*Size.*—5.5–8 cm across; mature leaf.

*Shape.*—Reniform, cordate base.

*Margin.*—Pedately lobed.

*Texture.*—Smooth; slightly reflective.

*Color.*—Top: Green group 137C; Bottom: Yellow-green group 146B.

*Ribs and veins.*—Palmate venation; Color: Yellow-green group 146C.

Petioles: 3–4.5 cm in length;

*Color.*—Yellow-green group 146B.

Stem:

*Color.*—Yellow-green group 146B.

*Internodes.*—2.5–5 cm in length.

THE BUD

Shape: Elliptical cluster; 4–9 buds per umbel.

Size: 2–2.5 cm across.

INFLORESCENCE

Blooming Habit: Continuous; free and early; upright.

Size: 5.5–7 cm across when fully opened.

Borne: Florets on pedicel; pedicel on peduncle; umbel 6–9 cm above foliage canopy.

Florets:

*Form.*—Flat to slightly cupped; semi-double.

*Color.*—Top: Red group 43A. Bottom: Red group 43C.

*Petals.*—10–13 in number, margin entire; separate, not united.

*Floret size.*—4–4.5 cm across.

*Texture and appearance.*—Smooth; semi-double floret containing 10–13 petals; appearance is a soft scarlet.

Petaloids:
*Quantity.*—2–3 in number.
*Shape.*—Twisted, elongated.
*Color.*—Red group 43B.
Pedicel: 1.5–2.5 cm in length.
*Color.*—Yellow-green group 146B.
Peduncle: 6–11 cm in length.
*Color.*—Yellow-green group 146A.
Disease resistance: Not known.
Lasting quality: A very heat tolerant variety that blooms continuously.

REPRODUCTIVE ORGANS

Stamens:
*Anthers.*—2–3 mm in length.
*Filaments.*—5–7 mm in length; white irregular shape.
*Pollen.*—Golden brown.
Pistils:
*Number.*—One.
*Length.*—8–10 mm.
*Stigma.*—5 or 6 parted. Color: Red group 39A.
*Style.*—3–4 mm in length; pale green.
Ovaries: Superior; pubescent; pale green; 4–5 mm in length, 2–3 mm across.
Fruit: None observed.

GENERAL CHARACTERISTICS

This new and distinct variety adds a new color to the Ivy Geranium class. The "Geranium" red color accents the medium green foliage.

This variety is also much hardier in higher temperatures than those Ivy Geraniums currently on the market.

Although similar in color to the variety Grenchen, Nanette is a true vining, ivy leaf Geranium with less upright growth and less leaf zoning than Grenchen.

We claim:

1. A new and distinct variety of Ivy Geranium plant as shown and described herein, and characterized by a new color to the Ivy Geranium class, a "Geranium" red color which accents the medium green foliage, and a variety which is also much hardier in higher temperatures than those Ivy Geraniums currently on the market.

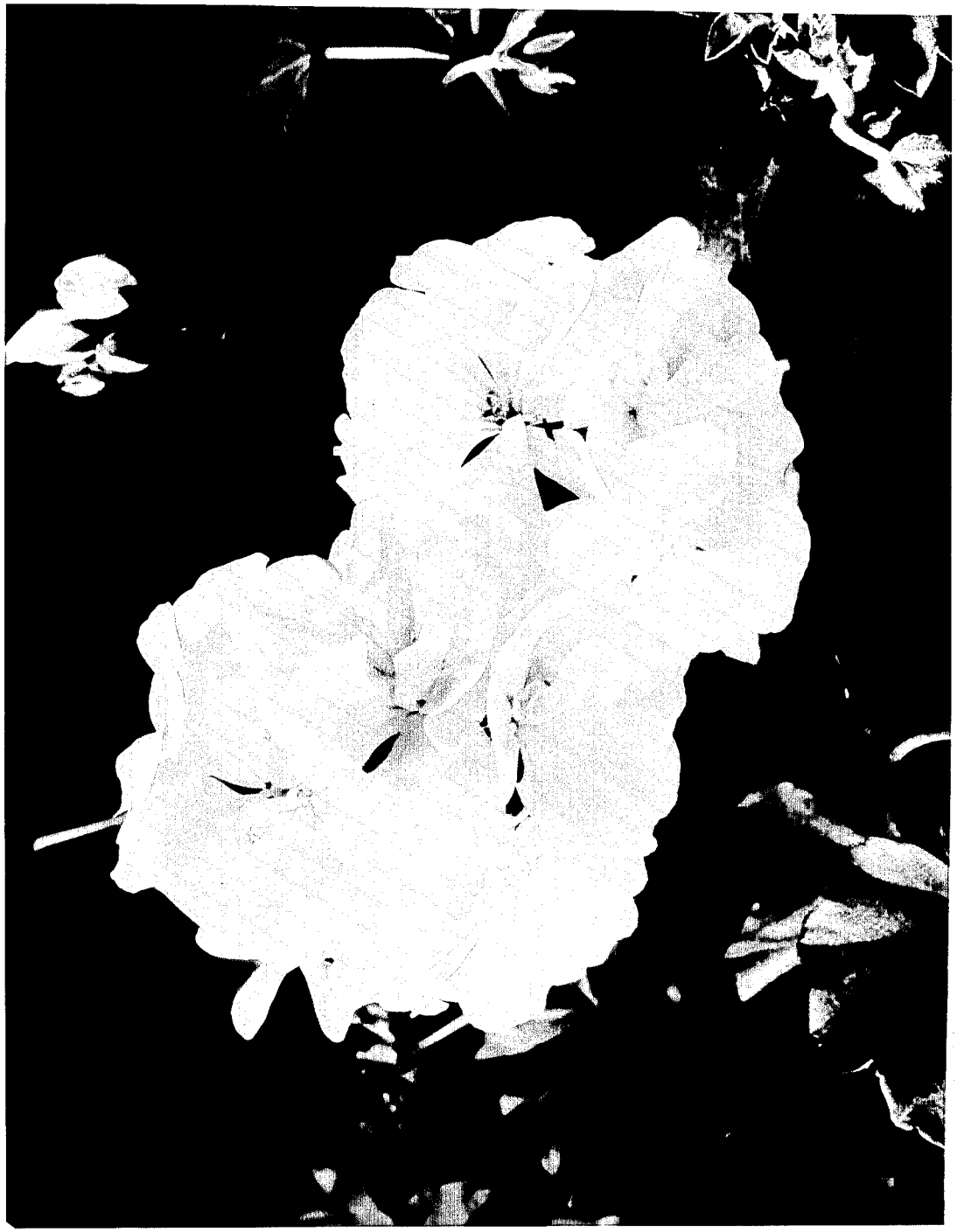

* * * * *